United States Patent [19]

Coats et al.

[11] 4,010,075

[45] Mar. 1, 1977

[54] PROCESS FOR PRODUCING 4-THIOURACIL

[75] Inventors: John H. Coats; Alma Dietz, both of Kalamazoo; Lester A. Dolak, Plainwell; Oldrich K. Sebek; Walter T. Sokolski, both of Kalamazoo, all of Mich.

[73] Assignee: The Upjohn Company, Kalamazoo, Mich.

[22] Filed: May 24, 1976

[21] Appl. No.: 689,376

[52] U.S. Cl. .............................................. 195/80 R
[51] Int. Cl.$^2$ .......................................... C12D 9/00
[58] Field of Search .................................. 195/80 R

[56] References Cited

OTHER PUBLICATIONS

Chemical Abstracts, vol. 82, 153744p; 1975.

*Primary Examiner*—A. Louis Monacell
*Assistant Examiner*—Robert J. Warden
*Attorney, Agent, or Firm*—Roman Saliwanchik

[57] ABSTRACT

A novel microbiological process for preparing 4-thiouracil, a known and useful compound. The compound is produced by the controlled fermentation of the new microorganism *Streptomyces libani* subsp. *soldani*, NRRL 8173, and its strains W and P having the NRRL designations NRRL 8174 and NRRL 8175, respectively.

8 Claims, No Drawings

PROCESS FOR PRODUCING 4-THIOURACIL

BACKGROUND OF THE INVENTION

The compound, 4-thiouracil, produced by the novel process of the subject invention has been known since about 1945. It has been described in the literature as an antibacterial, antitumor agent, useful in photographic processes and as a plant growth stimulator. The compound has been prepared in the prior art by chemical means. There is no known prior art which describes the production of 4-thiouracil by a microbiological process.

BRIEF SUMMARY OF THE INVENTION

The novel process of the subject invention produces a high yield of the compound 4-thiouracil. This process is conducted by culturing the new microorganism *Streptomyces libani* subsp. *soldani*, NRRL 8173, and its strains NRRL 8174 and NRRL 8175, in an aqueous nutrient medium under aerobic conditions. 4-Thiouracil is isolated from the fermentation beer by procedures generally known in the antibiotic art, for example, filtration, solvent extraction, partition chromatography, adsorption onto charcoal and the like.

DETAILED DESCRIPTION OF THE INVENTION

The compound produced by the novel process of the subject invention, 4-thiouracil, can be shown by the following structural formula:

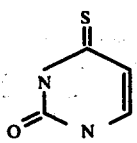

This compound is active against a variety of bacteria, for example, *Staphylococcus aureus*, *Bacillus subtilis*, *Escherichia coli*, and *Proteus vulgaris*. Accordingly, 4-thiouracil can be used in various environments to eradicate or control these microorganisms. For example, it can be used for treating breeding places of silkworms and to prevent or minimize infections caused by *Bacillus subtilis*. Since 4-thiourcil is active against *E. coli*, it can be used to reduce, arrest, and eradicate slime production in papermill systems caused by this microorganism.

THE MICROORGANISM

The microorganism used for the production of 4-thiouracil is *Streptomyces libani* subsp. *soldani*. A subculture of this microorganism can be obtained from the permanent collection of the Northern Regional Research Laboratory, U.S. Department of Agriculture, Peoria, Ill., U.S.A. Its accession number in this depository is NRRL 8173. It should be understood that the availability of the culture does not constitute a license to practice the subject invention in derogation of patent rights granted with the subject instrument by governmental action.

The microorganism of this invention was studied and characterized by Alma Dietz of the Upjohn Research Laboratories.

A new soil isolate NRRL 8173 has been compared with two strains and with the type culture *Streptomyces libani*. The new culture was considered to be most similar to *S. libani* in its color pattern on Ektachrome and in its microscopic characteristics. Detailed comparisons are given in Tables 1–5. A number of isolates of *S. libani* are characterized by Baldacci and Grein [Baldacci, E. and A. Grein. 1966. *Streptomyces avellaneus* and *Streptomyces libani*; two new species characterized by a hazel-nut brown (*avellaneus*) aerial mycelium. Giornale di Microbiologia 14: 185–198]. The characterizations reveal the natural variability of the culture. The same variability is noted between NRRL 8173 and the strains NRRL 8174 and NRRL 8175. *S. libani* var. *soldani* may be placed in the Gray series of Table 17.42f (Part 17. Actinomycetes and Related Organisms) of the Eighth Edition of Bergey's Manual of Determinative Bacteriology [Buchanan, R. E., and N. E. Gibbons. 1974. Bergey's Manual of Determinative Bacteriology, Eight Edition, The Williams and Wilkins Co., Baltimore]. The type culture, *S. libani*, is listed in Table 17.42f. An additional characterization of *S. libani* is found in Shirling and Gottlieb [Shirling, E. B. and D. Gottlieb. 1972. Cooperative description of type strains of *Streptomyces*. V. Additional descriptions. Int. J. Syst. Bacteriol. 22: 265–394]. Strong similarities are noted between the new soil isolate and *S. libani* in Tables 1–5 and in the references cited. The natural variability of the cultures and, in particular, the difference in antibiotic production require the new isolate to be considered a new subspecies. Therefore, in accordance with the rules set forth in the International Code of Nomenclature of Bacteria [International Code of Nomenclature of Bacteria, 1976 Revision. 1975. Edited by S. P. LaPage, p. H. A. Sneath, E. F. Lessel, V. B. D. Skerman, H. P. R. Seeliger and W. A. Clark. Published for the International Association of Microbiological Societies by the American Society for Microbiology, Washington, D.C.] the name *Streptomyces libani* subsp. *soldani* Dietz subsp. nova is proposed.

Color Characteristics

The cultures are melanin-negative and have white and gray aerial growth. Color characteristics of the cultures on Ektachrome are given in Table 1. Reference color characteristics are given in Table 2. The cultures may be placed in the White (W) or Gray (GY) color groups of Tresner and Backus [Tresner, H. D. and E. J. Backus. 1963. System of color wheels for streptomycete taxonomy. Appl. Microbiol. 11:335–338].

Microscopic Characteristics

Spores with a smooth surface are found in spiral spore chains. More than 10 spores occur per chain. The spore shape may be oval, reniform or spherical. Microscopic determinations were made following the procedures of Pridham et al. [Pridham, T. G., C. W. Hesseltine and R. G. Benedict. 1958. A guide for the classification of streptomycetes according to selected groups. Placement of strains in morphological sections. Appl. Microbiol. 6:52–79] and Dietz and Mathews [Dietz, A. and J. Mathews. 1971. Classification of Streptomyces spore surfaces into five groups. Appl. Microbiol. 21:527–533].

Cultural and Biochemical Characteristics

Cultural and biochemical characteristics are cited in Table 3.

Carbon Utilization

Carbon utilization is cited in Tables 4 and 5.

Temperature

The cultures grew well in the temperature range of 18°–37° C. Growth did not occur at 45° or 55° C. Media used for temperature studies were Bennett's, Czapek's sucrose, maltose-tryptone and Hickey-Tresner agars.

Antibiotic-Producing Properties

S. *libani* subsp. *soldani* NRRL 8173 produces 4-thiouracil. S. *libani* UC-5629 produces the libanomycin complex.

Source: Soil.
Type Culture: *Streptomyces libani* Baldacci and Grein, UC-5629, IMRU 3915.
Variety: *Streptomyces libani* subsp. *soldani* Dietz subsp. nova.
Strains: *Streptomyces libani* subsp. *soldani* strain W
*Streptomyces libani* subsp. *soldani* strain P

Table 1

Appearance of Streptomyces libani subsp. soldani NRRL 8173 and the Strains NRRL 8174 and NRRL 8175 vs. S. libani UC-5629 on Ektachrome*

| Agar Medium | Determination | NRRL 8173 | NRRL 8174 | NRRL 8175 | UC-5629 |
|---|---|---|---|---|---|
| Bennett's | S | White | Lavender-gray | Trace gray | Lavender-gray |
|  | R | Pale yellow cream | Yellow | Pale tan | Pale yellow-tan |
| Czapek's | S | White | White | Fair white | White |
| sucrose | R | Cream | Pale yellow | Pale tan | Pale yellow |
| Maltose | S | White | Gray white | Fair white | Lavender-gray |
| tryptone | R | Pale yellow | Yellow-tan | Pale yellow-tan | Pale yellow-tan |
| Peptone-iron | S | Trace white | Trace white | — | Trace lavender-gray |
|  | R | Yellow-tan | Yellow | Yellow-tan | Yellow |
| 0.1% Tyrosine | S | Trace white | Trace white | — | Trace lavender-gray |
|  | R | Red-pink | Red-pink | Deep red | Pale yellow |
| Casein starch | S | White | Pale gray | Pale cream | Trace lavender-gray |
|  | R | Very pale cream | Pale yellow | Lavender gray | Pale yellow |

*Dietz, A. 1954. Ektachrome transparencies as aids in actinomycete classification. Ann. N. Y. Acad. Sci. 60:152–154.
S = Surface R = Reverse
NOTE: "UC" is a registered trademark and refers to The Upjohn Company Culture Collection.

Table 2

Reference Color Characteristics of S. libani subsp. soldani vs. S. libani

ISCC-NBS Color-Name Charts Illustrated with Centroid Colors*
S. libani var. soldani

| Agar Medium | Determination | NRRL 8173 | | NRRL 8174 | |
|---|---|---|---|---|---|
| Bennett's | S | 86 l.Y under | Light Yellow | 93 y Gray | Yellowish gray |
|  |  | 214 p.V | Pale violet |  |  |
|  | R | 84 s.Y | Strong yellow | 89 p.Y | Pale yellow |
|  | P | 84 s.Y | Strong yellow | 90 gy.Y | Grayish yellow |
| Czapek's | S | 9 pk White | Pinkish white | 263 White | White |
| sucrose | R | 52 l.O | Light orange | 73 p.OY | Pale orange yellow |
|  | P | 28 l.y Pink | Light yellowish pink | 70 l.OY | Light orange yellow |
| Maltose- | S | 93 y Gray | Yellowish gray | 263 White | White |
| tryptone | R | 83 brill.Y | Brilliant yellow | 89 p.Y | Pale yellow |
|  | P | — |  | 71 m OY | Moderate orange yellow |
| Hickey- | S | 92 y White | Yellowish white | 9 pk White | Pink white |
| Tresner | R | 87 m.Y | Moderate yellow | 70 l.OY | Light orange yellow |
|  | P | — |  | 71 m OY | Moderate orange yellow |
| Yeast extract-malt extract (ISP-2) | S | 86 l.Y under | Light yellow | 263 White | White |
|  |  | 294 p.V | Pale violet |  |  |
|  | R | 91 d.gy.Y | Dark grayish yellow | 70 l.OY | Light orange yellow |
|  | P | — |  | — |  |
| Oatmeal (ISP-3) | S | 261 l.gy.p R | Light grayish purplish red | 93 y Gray | Yellowish gray |
|  | R | 89 p.Y | Pale yellow | 89 p.Y | Pale yellow |
|  | P | — |  | 90 gy.Y | Grayish yellow |
| Inorganic salts-starch (ISP-4) | S | 86 l.Y over | Light yellow | 93 y Gray | Yellowish gray |
|  |  | 244 p.r P | Pale reddish purple |  |  |
|  | R | 83 brill. Y | Brilliant yellow | 89 p.Y | Pale yellow |
|  | P | 87 m.Y | Moderate yellow | 90 gy.Y | Grayish yellow |
| Glycerol-asparagine (ISP-5) | S | 89 p.Y over | Pale yellow | 265 med. Gy | Medium gray |
|  |  | 261 l.gy.p R | Light grayish purplish red |  |  |
|  | R | 87 m.Y | Moderate yellow | 89 p.Y | Pale yellow |
|  | P | 87 m.Y | Moderate yellow | 90 gy.Y | Grayish yellow |

ISCC-NBS Color-Name Charts Illustrated with Centroid Colors*
S. libani var. soldani | S. libani

| Agar Medium | Determination | NRRL 8175 | | UC-5629 | |
|---|---|---|---|---|---|
| Bennett's | S | 93 y Gray | Yellowish gray | 93 y Gray | Yellowish gray |
|  | R | 70 l.OY | Light orange yellow | 67 brill.OY | Brilliant orange yellow |
|  | P | 67 brill.OY | Brilliant orange-yellow | 68 s.OY | Strong orange yellow |
| Czapek's | S | 92 y White | Yellowish white | 253 White | White |
| sucrose | R | 76 l.y Br | Light yellowish brown | 73 p.OY | Pale orange yellow |
|  | P | 77 l.y Br | Light yellowish brown | 29 m.y Pink | Moderate yellowish pink |
| Maltose- | S | 92 y White | Yellowish white | 93 y Gray | Yellowish gray |
| tryptone | R | 89 p.Y | Pale yellow | 83 brill. Y | Brilliant yellow |
|  | P | 76 l.y Br | Light yellowish brown | 84 s.Y | Strong yellow |

Table 2-continued

Reference Color Characteristics of S. libani subsp. soldani vs. S. libani

| | | | | | | | |
|---|---|---|---|---|---|---|---|
| Hickey-Tresner | S | 92 | y White | Yellowish white | 9 | pk White | Pinkish white |
| | R | 73 | p.OY | Pale orange yellow | 73 | p.O | Pale orange yellow |
| | P | 76 | l.y Br | Light yellowish brown | 67 | brill.OY | Brilliant orange yellow |
| Yeast extract-malt extract (ISP-2) | S | 9 | pk White | Pinkish white | 263 | White | White |
| | R | 57 | l.Br | Light brown | 70 | l.OY | Light orange yellow |
| | P | 42 | l.r Br | Light reddish brown | 71 | m.OY | Moderate orange yellow |
| Oatmeal (ISP-3) | S | 93 | y Gray | Yellowish gray | 93 | y Gray | Yellowish gray |
| | R | 70 | l.OY | Light orange yellow | 89 | p.Y | Pale yellow |
| | P | 71 | m.OY | Moderate orange yellow | 101 | l.Gray | light gray |
| Inorganic salts-starch (ISP-4) | S | 92 | y White | Yellowish white | 81 | d.gy.yBr | Dark grayish yellowish brown |
| | R | 70 | l.OY | Light orange yellow | 73 | p.OY | Pale orange yellow |
| | P | 71 | m.OY | Moderate orange yellow | 73 | d.OY | Dark orange yellow |
| Glycerol-asparagine (ISP-5) | S | 93 | y Gray | Yellowish gray | 9 | pk White | Pinkish white |
| | R | 70 | l.OY | Light orange yellow | 73 | p.OY | Pale orange yellow |
| | P | 71 | m.OY | Moderate orange yellow | 71 | m.OY | Moderate orange yellow |

*Kelly, K. L. and D. B. Judd. 1955. The ISCC-NBS method of designating colors and a dictionary of color names. U.S. Dept. Comm. Circ. 553.
S = Surface  R = Reverse  P = Pigment Table 3

Cultural and Biochemical Characteristics

| Medium | Determination | S. libani subsp. soldani NRRL 8173 | NRRL 8174 | NRRL 8175 | S. libani UC-5629 |
|---|---|---|---|---|---|
| Agar | | | | | |
| Peptone-iron | S | — | White | — | Trace pale gray |
| | R | Colorless | Yellow | Yellow-tan | Pale cream-tan |
| | P | — | — | — | — |
| | O | Melanin negative | Melanin negative | Melanin negative | Melanin negative |
| Calcium malate | S | Fair white | Trace white | — | Trace pale gray |
| | R | White or colorless | Colorless | Colorless | Colorless or pale gray |
| | P | — | — | — | — |
| | O | Malate solubilized | Malate not solubilized | Malate not solubilized | Malate not solubilized |
| Glucose asparagine | S | Cream | White with trace gray | Trace white | Pale gray-white |
| | R | Pink-tan | Cream | Pale tan | Pale cream-pink |
| | P | Pink | — | Trace pink | Pale pink |
| Skim milk | S | Trace white on edge | White on edge | — | Pale gray-white |
| | R | Pink-orange | Colorless | Colorless and trace orange | Orange-tan |
| | P | Pink-orange | — | — | Orange-tan |
| | O | Casein hydrolyzed | Casein not hydrolyzed | Casein not hydrolyzed to trace hydrolyzed around growth | Casein not hydrolyzed |
| Tyrosine | S | Gray | Pale cream-pink | — | Pale cream-white |
| | R | Red-tan | Light red-tan | Red-tan | Yellow |
| | P | Red-tan | Light red-tan | Red-tan | Pale yellow |
| | O | Tyrosine solubilized | Tyrosine solubilized | Tyrosine solubilized | Tyrosine solubilized |
| Xanthine | S | Cream white | Pale cream white | Fair pale gray | Cream white |
| | R | Cream | Cream | Cream | Pale yellow |
| | P | Pale cream | Pale cream | Cream | Pale yellow |
| | O | Xanthine not solubilized | Xanthine not solubilized | Xanthine solubilized | Xanthine solubilized |
| Nutrient starch | S | Cream white | Cream white | — | Cream white |
| | R | Cream | Cream | Cream | Pale yellow |
| | P | — | Pale Cream | Pale cream | — |
| | O | Starch solubilized | Starch solubilized | Starch solubilized | Starch solubilized |
| Yeast extract-malt extract | S | Cream | Pale gray-cream | — | Pale gray-cream |
| | R | Yellow-tan | Pale cream-brown | Pale yellow-tan | Yellow-tan |
| | P | — | Pale olive-gray | Pale yellow-tan | Yellow-tan |
| Peptone-yeast extract-iron (ISP-6) | S | White | Cream white | — | Very pale gray-white |
| | R | Yellow | Pale tan | Yellow-tan | Yellow-tan |
| | P | — | — | Pale yellow-tan | Yellow-tan |
| L-Tyrosine (ISP-7) | S | Lavender-gray-white | Lavender-gray-cream with black exudate | Pale lavender-gray-cream | Cottony pale-gray with white flecks |
| | R | Pale tan | Pale olive | Olive-tan | Cream-tan (reddish at base |
| | P | Pale tan | Pale olive | Pale olive-tan | — |
| Gelatin | | | | | |
| Plain | S | Colorless surface ring | White surface pellicle | Colorless surface ring | Colorless surface ring |
| | P | — | Olive | — | Olive brown to olive |
| | O | Liquefaction complete | No liquefaction | No liquefaction | Liquefied in olive-brown area = trace liquefaction |
| Nutrient | S | Colorless surface ring | White surface pellicle | Colorless surface ring | Colorless surface ring |
| | P | — | Pale tan | — | — |
| | O | Liquefaction | No liquefaction | No liquefaction | No liquefaction |

Table 3-continued

| Medium | Determination | Cultural and Biochemical Characteristics S. libani subsp. soldani NRRL 8173 | NRRL 8174 | NRRL 8175 | S. libani UC-5629 |
|---|---|---|---|---|---|
| Nitrate Broth | | complete | | | |
| Synthetic | S | White aerial on surface ring | — | — | — |
| | P | — | — | — | — |
| | O | Trace flocculent bottom growth | Trace flocculent bottom growth | Flocculent bottom growth | Compact bottom growth |
| Synthetic | O | Nitrate not reduced Red with Zn dust | Nitrate not reduced Red with zn dust | Nitrate not reduced Red with zn dust | Nitrate not reduced Red with zn dust |
| Nutrient | S | Trace white aerial growth on surface ring | Pale gray-white aerial growth on surface ring | — | — |
| | P | — | — | — | — |
| | O | Flocculent bottom growth Nitrate not reduced Orange with Zn dust | Flocculent bottom growth Nitrate not reduced Orange with zn dust | Pelliate like bottom growth Nitrate not reduced Orange with zn dust | Flocculent bottom growth Nitrate not reduced Orange with zn dust |
| Litmus milk | S | Pale gray-pink aerial growth on pink-maroon surface ring | Pale lavender-gray aerial growth on pale salmon surface ring | — | Pale gray-pink aerial growth reddish-purple surface ring |
| | P | — | — | — | — |
| | O | Peptonization ¾ Litmus reduced and coagulation ⅓ pH 6.5 | No peptonization Litmus changed to lavender gray pH 7.1 | Peptonization ¾ pH 6.5 | Peptonization ¾ Partial decolorization pH 6.7 |

S = Surface
R = Reverse
P = Pigment
O = Other characteristics

Table 4

Growth on Carbon Compounds in the Synthetic Medium of Pridham and Gottlieb*

| | | S. libani subsp. soldani | | | S. libani |
|---|---|---|---|---|---|
| | | NRRL 8173 | NRRL 8174 | NRRL 8175 | UC-5629 |
| CONTROL | | + | (−) | (−) | (+) |
| 1. | D-Xylose | + | + | + | + |
| 2. | L-Arabinose | + | (+) | (+) | (+) |
| 3. | Rhamnose | + | (−) | (−) | (+) |
| 4. | D-Fructose | + | + | + | + |
| 5. | D-Galactose | + | + | + | + |
| 6. | D-Glucose | + | + | + | + |
| 7. | D-Mannose | + | + | + | + |
| 8. | Maltose | + | + | + | + |
| 9. | Sucrose | + | + | + | + |
| 10. | Lactose | + | (−) | (−) | + |
| 11. | Cellobiose | + | (−) | (−) | (+) |
| 12. | Raffinose | + | + | + | + |
| 13. | Dextrin | + | + | + | + |
| 14. | Inulin | + | (−) | (−) | (+) |
| 15. | Soluble Starch | + | + | + | + |
| 16. | Glycerol | + | + | + | + |
| 17. | Dulcitol | (+) | (−) | (−) | (+) |
| 18. | D-Mannitol | + | + | + | + |
| 19. | D-Sorbitol | (+) | + | + | + |
| 20. | Inositol | + | + | + | + |
| 21. | Salicin | (−) | — | — | — |
| 22. | Phenol | — | — | — | — |
| 23. | Cresol | — | — | — | — |
| 24. | Na Formate | — | — | — | — |
| 25. | Na Oxalate | (+) | (−) | (−) | (−) |
| 26. | Na Tartrate | (+) | (−) | (−) | — |
| 27. | Na Salicylate | — | — | — | — |
| 28. | Na Acetate | (+) | (+) | (+) | (+) |
| 29. | Na Citrate | + | (+) | (+) | (+) |
| 30. | Na Succinate | + | (+) | (+) | (+) |

*Pridham, T. G. and D. Gottlieb. 1948. The utilization of carbon compounds by some Actinomycetales as an aid for species determination. J. Bacteriol. 56: 107–114.
+ = Good growth
(+) = Moderate growth
(−) = Poor growth
— = No growth

Table 5

Growth on Carbon Compounds in the Synthetic Medium of Shirling and Gottlieb *

| CONTROL | S. libani subsp. soldani | | | S. libani |
|---|---|---|---|---|
| | NRRL 8173 | NRRL 8174 | NRRL 8175 | UC-5629 |
| Negative (synthetic medium only) | + | − | − | + |
| Positive (synthetic medium with D-glucose) | + | + | + | + |
| 1. Arabinose | + | + | + | ++ |
| 2. Sucrose | ++ | ++ | ++ | ++ |
| 3. D-Xylose | ++ | + | ++ | + |
| 4. Inositol | ++ | ++ | ++ | ++ |
| 5. D-Mannitol | + | ++ | ++ | ++ |
| 6. D-Fructose | + | + | ++ | ++ |
| 7. Rhamnose | + | ± | − | − |
| 8. Raffinose | ++ | ± | ± | + |
| 9. Cellulose | − | − | − | − |

* Shirling, E. B. and D. Gottlieb. 1966. Methods for characterization of Streptomyces species. Int. J. Syst. Bacteriol.

4-Thiouracil is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solubles solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of 4-thiouracil can be effected at any temperature conducive to satisfactory growth of the micro-organism, for example, between about 18° and 40° C., and preferably between about 20° and 28° C. Ordinarily, optimum production of the compound is obtained in about 3 to 15 days. The medium normally remains acidic during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of 4-thiouracil and the attendant inefficient utilization of the equipment. Accordingly, it is desirable to produce a vegetative inoculum in a nutrient broth culture by inoculating this broth culture with an aliquot from a soil, agar plug, stored frozen above liquid $N_2$, or a slant culture. When a young, active vegetative inoculum has thus been secured, it is transferred aseptically to large vessels or tanks. The medium in which the vegetative inoculum is produced can be the same as, or different from, that utilized for the production of 4-thiouracil, so long as a good growth of the microorganism has been obtained.

A variety of procedures can be employed in the isolation and purification of 4-thiouracil from fermentation beers, for example, solvent extraction, partition chromatography, silica gel chromatography, liquid-liquid distribution in a Craig apparatus, adsorption on resins, and crystallization from solvents.

In a preferred recovery process 4-thiouracil is recovered from its culture medium by separation of the mycelia and undissolved solids by conventional means, such as by filtration or centrifugation. The antibiotic is then recovered from the filtered or centrifuged broth by extraction. For the extraction of 4-thiouracil from the filtered broth, water-immiscible organic solvents in which it is soluble, for example, chloroform, ethylene dichloride, ethyl acetate (preferred), and methylene chloride can be used. Advantageously, the extraction is carried on after the filtered beer is adjusted to an approximate pH 7.0 with a mineral acid. The solvent extracts are combined and evaporated to dryness under vacuum. Alternately, 4-thiouracil can be recovered from the filtered fermentation beer by use of a resin which comprises a non-ionic macroporous copolymer of styrene crosslinked with divinylbenzene. Resins of this type are disclosed in U.S. Pat. No. 3,515,717. Examples of this type of resin are Amberlite XAD-2, XAD-4, XAD-12. These resins can be obtained from the Rohm and Haas Chemical Company. Further, anion exchange resins can be used to recover 4-thiouracil from the filtered fermentation broth. Examples of such resins are Dowex-1 and Dowex-2 in the hydroxide form. These resins can be obtained from the Dow Chemical Company. When an anion exchange resin is used in the recovery process, the 4-thiouracil can be eluted from the resin by adding a polar, water-miscible solvent to the aqueous stream. Examples of such solvents are acetone, methanol, i-propanol, ethanol, dioxane or tetrahydrofuran. The organic solvent can then be removed in vacuo and the 4-thiouracil extracted from the aqueous using one or more of the above solvents. If a solid forms on removal of the organic solvent, then the product can be recovered by filtration or lyophilization. A further alternate recovery process is to pass the filtered beer over activated charcoal and eluting the 4-thiouracil, as described above.

Purification of the 4-thiouracil preparation, obtained as described above, can be achieved by the use of silica gel or alumina chromatography using a pair of compatible lipophilic and hydrophilic solvents such as CHCl$_3$/MeOH, CHCl$_3$/EtOH, EtOAc/acetone, BuOAc/MeOH, EtOAc/MeOH (preferred), and the like.

Hereinafter are described non-limiting examples of the process of the subject invention. All percentages are by weight and all solvent mixture proportions are by volume unless otherwise noted.

EXAMPLE 1

Part A. Fermentation

One agar plug of *Streptomyces libani* subsp. *soldani*, NRRL 8173, stored above liquid nitrogen, is used to inoculate each of a series of 500-ml Erlenmyer flasks each containing 100 ml of sterile seed medium consisting of the following ingredients:

| Glucose monohydrate | 25 | g/liter |
|---|---|---|
| Pharmamedia * | 25 | g/liter |
| Tap water q.s. | 1 | liter |

* Pharmamedia is an industrial grade of cottonseed flour produced by Traders Oil Mill Company, Fort Worth, Texas.

The seed medium presterilization pH is 7.2. The seed inoculum is grown for 3 days at 28° C. on a Gump rotary shaker operating at 250 r.p.m. and having a 2½ inch stroke.

Seed inoculum (5%), prepared as described above, is used to inoculate a series of 500 ml fermentation flasks, each containing 100 ml of sterile fermentation medium consisting of the following ingredients:

| Glycerol | 10 g/liter |
|---|---|
| Yeast Extract | 2.5 g/liter |
| Brer Rabbit Molasses | 10 g/liter |
| Tryptone * | 5 g/liter |
| Tap water q.s. | 1 liter |

* Difco Laboratories, Detroit, Michigan.

The inoculated fermentation flasks are incubated at a temperature of 28° C. for 5 days while being shaken on a Gump rotary shaker operating at 250 r.p.m. and having a 2½ inch stroke. Foaming in the fermentation flasks is controlled by the antifoam agent UCON (a synthetic defoamer supplied by Union Carbide, N.Y., N.Y.). A representative 5-day fermentation has the following titers of antibiotic in the fermentation broth:

| Day | Assay, BU/ml |
|---|---|
| 2 | 6.7 |
| 3 | 15.0 |
| 4 | 10.0 |
| 5 | 16.0 |

The assay is a disc plate biounit assay using the bacterium *Bacillus subtilis* grown on a synthetic medium. The synthetic medium has the following composition:

| Na$_2$HPO$_4$ · 7H$_2$O | 1.7 g |
|---|---|
| KH$_2$PO$_4$ | 2.0 g |
| (NH$_4$)$_2$SO$_4$ | 1.0 g |
| MgSO$_4$ | 0.1 g |
| Glucose | 2.0 g |
| Bacto Agar * | 15.0 g |
| Distilled water | 1 liter |
| Metallic ion stock solution ** | 1 ml |

* Bacto Agar obtained from Difco Laboratories, Detroit, Michigan.
** Metallic ion stock solution consists of the following:

| NaMoO$_4$ · 2H$_2$O | 200 µg/ml |
|---|---|
| CoCl$_2$ | 100 µg/ml |
| CuSO$_4$ | 100 µg/ml |
| MnSO$_4$ | 2 mg/ml |
| CaCl$_2$ | 25 mg/ml |
| FeCl$_2$ · 4H$_2$O | 5 mg/ml |
| ZnCl$_2$* | 5 mg/ml |

* ZnCl$_2$ has to be dissolved separately using a drop of 0.1N HCl for 10 ml of water. The stock solution is heated to bring all the compounds in solution, kept standing for 24 hours, and sterile filtered.

This medium is inoculated with a spore suspension of *B. subtilis* ($1.5 \times 10^{10}$ cells/ml) at a rate of 0.5 ml/liter. The beer samples are applied to 12.5 mm diameter adsorbent paper discs (0.08 ml/disc), which are then applied to the surface of the assay plate. The assay system is incubated overnight at 37° C., and the zones of inhibition are measured. The potency of the sample is related to the diameter of the inhibition zone by means of the usual standard curve.

A biounit (BU) is defined as the concentration of the antibiotic which gives a 20 mm zone of inhibition under the above assay conditions. Thus, if for example a fermentation beer, or other solution containing the antibiotic, needs to be diluted 1/100 to give a 20 mm zone of inhibition, the potency of such beer or solution is 100 BU per ml.

Part B. Recovery

Whole fermentation beer (800 ml) at pH 8.0 is filtered with the aid of diatomaceous earth as a filter aid after the adjustment to pH 7.0 with 3N HCl. The resulting 750 ml of filtrate is extracted twice with 2-750 ml portions of ethyl acetate. The organic phases are combined, washed with a saturated sodium chloride solution, dried with magnesium sulfate, filtered and concentrated on a rotary evaporator; yield 166.0 mg of a preparation of 4-thiouracil.

Part C. Purification

A preparation of 4-thiouracil (116 mg), prepared as described above, is dissolved in about 5 ml of ethyl acetate and the solution is injected via a syringe onto a size C Merck pre-packed column of silica gel. The column is developed isocratically at 5 ml/min. to tube 35 whereupon the solution is switched to 10:1 EtOAc:MeOH (v/v). The 25 ml fractions are assayed by dipping 12.7 mm pads and placing them onto agar trays seeded with *Salmonella schottmuelleri*. The trays are incubated for 18 hours at 32° C. and the zones are read. Tubes 23–28 which give zones ranging from 24–38 mm are combined. Concentration of this pool gives 112.2 mg. of essentially pure 4-thiouracil.

EXAMPLE 2

By substituting *Streptomyces libani* subsp. *soldani*, strain W, NRRL 8174 for *S. libani* subsp. *soldani*, NRRL 8173 in Example 1, there is obtained 4-thiouracil which can be recovered in the essentially pure form by the procedures disclosed in Example 1.

EXAMPLE 3

By substituting *Streptomyces libani* subsp. *soldani*, strain P, NRRL 8175 for *S. libani* subsp. *soldani*, NRRL 8173 in Example 1, there is obtained 4-thiouracil which can be recovered in the essentially pure form by the procedures disclosed in Example 1.

We claim:

1. A process for preparing 4-thiouracil which comprises cultivating *Streptomyces libani* subsp. *soldani*, having the identifying characteristics of NRRL 8173 in an aqueous nutrient medium under aerobic conditions until substantial antibiotic activity is imparted to said medium.

2. A process, according to claim 1, wherein said aqueous nutrient medium contains a source of assimilable carbohydrate and assimilable nitrogen.

3. A process for recovering 4-thiouracil from a 4-thiouracil fermentation beer which comprises:
   1. filtering a 4-thiouracil containing fermentation beer to obtain a clear beer;
   2. extracting said clear beer with an organic solvent in which 4-thiouracil is soluble to obtain solvent extracts containing 4-thiouracil;
   3. chromatographing said solvent extract on a silica gel column to obtain fractions containing 4-thiouracil; and
   4. concentrating said fractions to give an essentially pure preparation of 4-thiouracil.

4. A process, according to claim 3, wherein the silica gel column is eluted with a solvent system consisting of ethyl acetate and methanol (10:1).

5. A process for preparing 4-thiouracil which comprises cultivating *Streptomyces libani* subsp. *soldani*, strain W, having the identifying characteristics of NRRL 8174 in an aqueous nutrient medium under aerobic conditions until substantial antibiotic activity is imparted to said medium.

6. A process, according to claim 5, wherein said aqueous nutrient medium contains a source of assimilable carbohydrate and assimilable nitrogen.

7. A process for preparing 4-thiouracil which comprises cultivating *Streptomyces libani* subsp. *soldani*, strain P, having the identifying characteristics of NRRL 8175 in an aqueous nutrient medium under aerobic conditions until substantial antibiotic activity is imparted to said medium.

8. A process, according to claim 7, wherein said aqueous nutrient medium contains a source of assimilable carbohydrate and assimilable nitrogen.

* * * * *

UNITED STATES PATENT OFFICE
CERTIFICATE OF CORRECTION

Patent No. 4,010,075      Dated March 1, 1977

Inventor(s) John H. Coats, Alma Dietz, Lester A. Dolak, Oldrich K. Sebek and Walter T. Sokolski It is certified that error appears in the above-identified patent and that said Letters Patent are hereby corrected as shown below:

Front page, left column, for "689,376" read -- 689,367 --.

Column 2, line 32, for "p.H.A." read -- P.H.A. --.

Column 8, Table 3 - under S. libani
                UC-5629 for "aerial growth" read -- aerial growth on --.

Signed and Sealed this

Third Day of May 1977

[SEAL]

Attest:

RUTH C. MASON
*Attesting Officer*

C. MARSHALL DANN
*Commissioner of Patents and Trademarks*